(12) United States Patent
Brock-Fisher

(10) Patent No.: US 6,716,171 B1
(45) Date of Patent: Apr. 6, 2004

(54) SYSTEM AND METHOD FOR INTERFACING AN ULTRASOUND TRANSDUCER WITH A COMPUTING DEVICE PERFORMING BEAMFORMING PROCESSING

(75) Inventor: George Brock-Fisher, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/261,890

(22) Filed: Sep. 30, 2002

(51) Int. Cl.$^7$ .................................................. A61B 8/00
(52) U.S. Cl. ....................................................... 600/443
(58) Field of Search ................................ 600/437, 443, 600/447; 128/916

(56) References Cited

U.S. PATENT DOCUMENTS

| | | | | |
|---|---|---|---|---|
| 5,795,297 A | * | 8/1998 | Daigle ........................ | 600/447 |
| 6,350,239 B1 | * | 2/2002 | Ohad et al. ................. | 600/437 |
| 6,440,071 B1 | * | 8/2002 | Slayton et al. .............. | 600/437 |
| 6,475,146 B1 | * | 11/2002 | Freiburger et al. .......... | 600/437 |
| 6,491,634 B1 | * | 12/2002 | Leavitt et al. ............... | 600/447 |
| 6,500,120 B1 | * | 12/2002 | Anthony et al. ............. | 600/437 |
| 6,526,163 B1 | * | 2/2003 | Halmann et al. ............ | 382/128 |
| 6,530,887 B1 | * | 3/2003 | Gilbert et al. ............... | 600/459 |
| 6,569,097 B1 | * | 5/2003 | McMorrow et al. ......... | 600/437 |
| 2003/0097071 A1 | * | 5/2003 | Halmann et al. ............ | 600/459 |

* cited by examiner

*Primary Examiner*—Francis J. Jaworski
(74) *Attorney, Agent, or Firm*—John Vodopia

(57) ABSTRACT

A beamformer for an ultrasound imaging system is provided, the ultrasound imaging system having a probe having a transducer array for transmitting and receiving analog signals, and a personal computer. The beamformer includes a beamformer software application module configured for execution by the computing device for performing at least partial beamforming processing on digital data transmitted between the transducer array and the computing device, and means for exchanging signals and data between the transducer array and the computing device and performing at least one of A/D and D/A conversions on the exchanged signals and data. In the preferred embodiment, the beamformer further includes a module integrated within architecture of the computing device, wherein the integrated module is preferably Random Access Memory (RAM) included in storage means of the computing device. A method is further provided for performing a transmit beamforming process in an ultrasound system having a computing device and a probe including a transducer array, the method including the steps of performing transmit beamforming processing in the computing device in accordance with transmit settings to generate digital transmit data, storing the digital transmit in the data storage memory, retrieving the digital transmit data from the storage memory, converting the digital transmit data to analog transmit signals, and transmitting the analog transmit signals to the transducer array. A method is further provided for performing a receive beamforming process in an ultrasound system having a computing device including storage memory, an interface module and a probe including a transducer array, the method including the steps of receiving analog signals from the transducer array, converting the analog signals to digital data, storing the digital data in the storage memory, retrieving the digital data from the storage memory, and performing receive beamforming operations on the digital data by the computing device.

20 Claims, 4 Drawing Sheets

SYSTEM AND METHOD FOR INTERFACING AN ULTRASOUND TRANSDUCER WITH A COMPUTING DEVICE PERFORMING BEAMFORMING PROCESSING

FIELD OF THE INVENTION

The present invention generally relates to beamforming in ultrasound imaging systems, and in particular to a system and method for interfacing an ultrasound transducer with a computing device that performs beamforming processing.

BACKGROUND OF THE INVENTION

Ultrasound diagnostic technology generally relates to imaging of biological tissue by transmitting ultrasonic waves into tissue of a body being imaged, and receiving and processing ultrasonic wave echoes reflected from the tissue. An ultrasonic imaging system typically includes a transducer array provided within a probe, a beamformer and a display/user interface subsystem. The transducer array couples the acoustic energy into and out of the body, and converts the received waves into electrical signals ready for processing. The display subsystem processes and displays received signals. The user interface provides means for allowing a user to enter commands for controlling components of the system. The beamformer includes a transmit beamformer which controls operation of the transducer array for forming the transmitted acoustic energy into a directed beam in the body being imaged, and a receive beamformer for processing the received echoes for forming lines of data ready for processing by the display subsystem.

The beamformer has been implemented in a wide variety of technologies. For example, initially receive beamformers were implemented in analog electronics for performing fundamental delay and sum operations. As it became cost effective to do so beamformer design migrated to digital technology, in which the received RF signals were converted to digital format by A/D converters. The high-speed digital data was subsequently processed in dedicated VLSI devices.

With the evolving development of digital technologies and personal computers, portions of the display/user interface subsystem and the beamformer functions have been implemented directly in a computing device such as a personal computer (PC). The ability to upgrade PC hardware while maintaining software compatibility over generations of hardware upgrades is one of the advantages achieved by incorporation of the beamformer into the PC, in addition to integration with the display/user interface subsystem. However, the incorporation of the beamformer into the PC is limited due to the large data bandwidth, for example 128 channels of high speed RF data, processed by the beamformer.

Personal computers have architectures characterized by one or more central processors or microprocessors. These processors communicate to external devices by means of input/output (I/O) interface cards, which provide for the unique requirements of differing peripheral devices such as monitors, keyboards, etc. These peripheral devices are characterized by low data bandwidth relative to the needs of an ultrasound beamformer. Beamformer incorporation into the PC has required processing of the high speed RF data by external hardware devices for performing mathematical operations and convergence of the data into a narrow data stream provided to the PC via an I/O slot. However, the external hardware is expensive, requires custom design and manufacture for individual applications, and is limited in its ability to expand and adapt.

SUMMARY OF THE INVENTION

A beamformer for an ultrasound imaging system is provided, the ultrasound imaging system having a probe having a transducer array for transmitting and receiving analog signals, and a personal computer. The beamformer includes a beamformer software application module configured for execution by the computing device for performing at least partial beamforming processing on digital data transmitted between the transducer array and the computing device, and means for exchanging signals and data between the transducer array and the computing device and performing at least one of A/D and D/A conversions on the exchanged signals and data. In the preferred embodiment, the beamformer further includes a module integrated within architecture of the computing device, wherein the integrated module is preferably Random Access Memory (RAM) included in storage means of the computing device. The means for exchanging signals includes an interface module coupled between the transducer array and the computing device for performing the conversions. A method is further provided for performing a transmit beamforming process in an ultrasound system having a computing device and a probe including a transducer array, the method including the steps of performing transmit beamforming processing in the computing device in accordance with transmit settings to generate digital transmit data, storing the digital transmit in the data storage memory, retrieving the digital transmit data from the storage memory, converting the digital transmit data to analog transmit signals, and transmitting the analog transmit signals to the transducer array. A method is further provided for performing a receive beamforming process in an ultrasound system having a computing device including storage memory, a interface module and a probe including a transducer array, the method including the steps of receiving analog signals from the transducer array, converting the analog signals to digital data, storing the digital data in the storage memory, retrieving the digital data from the storage memory, and performing receive beamforming operations on the digital data by the computing device.

BRIEF DESCRIPTION OF THE DRAWINGS

Various embodiments of the invention will be described herein below with reference to the figures wherein.

DESCRIPTION OF THE PREFERRED EMBODIMENTS

Figure 1:
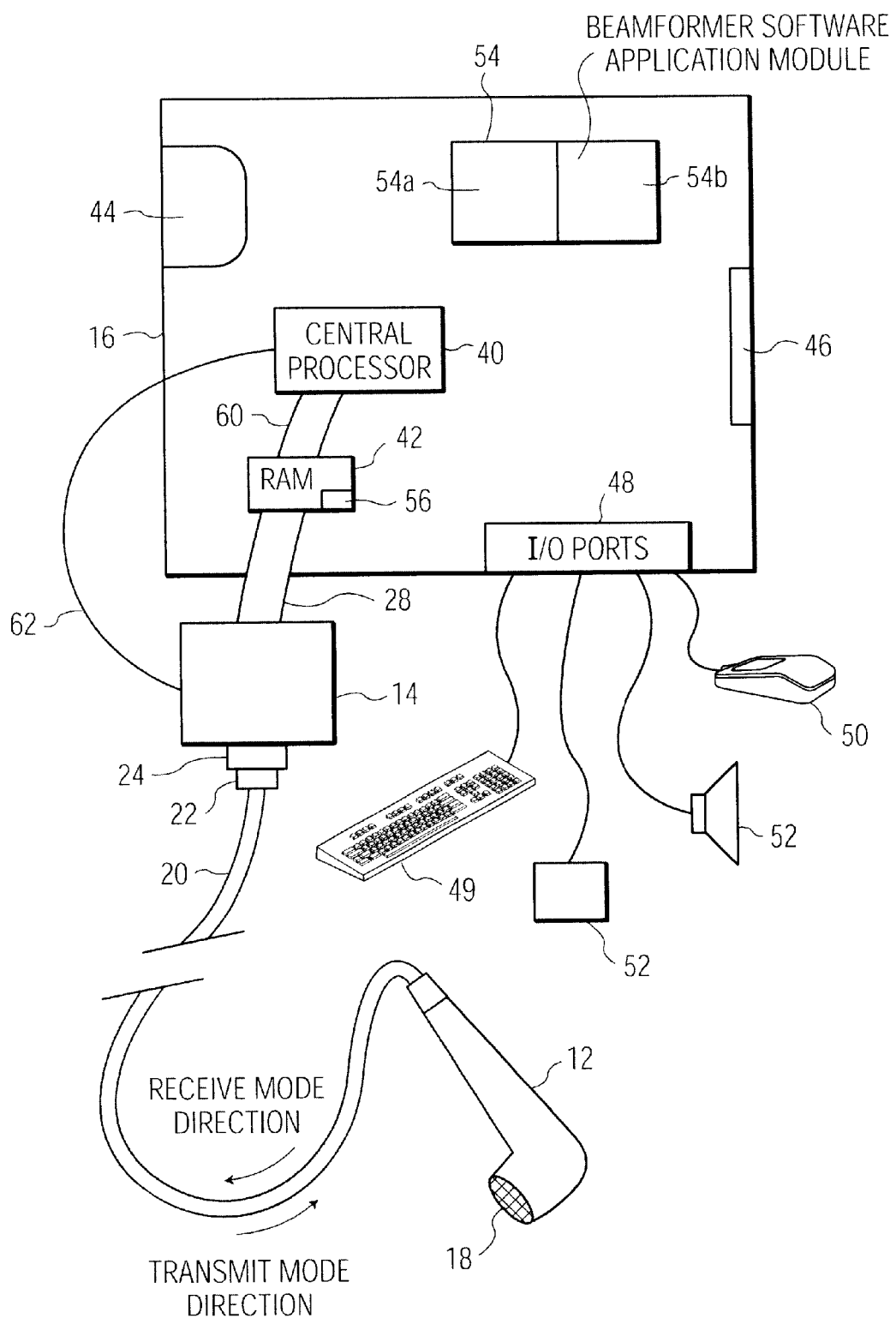
FIG. 1 is a schematic representation of an ultrasonic system having an interface in accordance with an embodiment of the present invention.

With reference to FIG. 1, an ultrasound imaging system 10 is shown, including a probe 12, [GLOBAL] interface module 14 and computing device 16. The probe 12 includes a commercially available array 18 of transducer elements, such as a single array, or a double array, and a static array or a mechanical array in accordance with design choice. The transducer array 18 may include a transmit transducer array and a receive transducer array, or the elements of the transducer array 18 may alternately perform transmit and receive functions. The interface module 14 interfaces the transducer array 18 to computing device 16. The probe 12 communicates with the interface module 14 via a transducer cable 20 which couples to the interface module 14 via transducer connector 22 of cable 18 and cable connector 24 of interface module 14. The interface module 14 connects with the computing device 16 via high bandwidth connector 28. The interface module 14 is external to the computing device architecture, but may be internal to its physical structure by being enclosed within a housing of the computing device 16. Preferably the interface module 14 is housed within a housing of computing device 16.

The computing device 16 includes a central processor 40, including one or more processors, connected at least to memory components and optional peripheral devices via I/O ports 48. The computing device 16 is a device such as a personal computer (PC), a cellular telephone, a PDA, or other device having one or more microprocessors coupled to one or more memory components. The memory components include, for example, a high bandwidth memory 42 communicating with the central processor via a high bandwidth connection, such as Random Access Memory (RAM), and relatively low bandwidth memory components, such as hard drive 44 and external memory components (i.e. floppy discs, compact discs (CDs), etc.) connected via external memory drive(s) 46. Peripheral devices may include devices such as a keyboard 49, mouse 50, display 52, printer 54, etc.

An integrated module 56 integrated into the high bandwidth memory 42 is further provided for storing data exchanged between the interface module 14 and the computing device 16. The integrated module 56 thus integrated into the internal architecture of the computing device 16 has sufficient bandwidth and volume for accommodating reading and writing a high bandwidth and volume of data being processed in real time by the beamformer application software module 54, in at least one of a transmit mode and a receive mode The integrated module 54 is preferably allocated specifically for use by the beamformer application software module 54.

Preferably the computing device 16 is a commercially available personal computer having a commercially available interface standard for providing communication between the central processor 40 and the high bandwidth memory 42. Preferably, the high bandwidth memory 42 is a RAM module, and the integrated module 54 is included in the RAM module. The high bandwidth capabilities of RAM provide the beamformer application software module 54 with the ability to perform beamformer transmit operations for controlling multiple elements of the transducer array 18, and perform receive beamformer operations on received echo data on a virtual real time basis for preparing the data for display for a virtual real time display of the area being imaged.

A beamformer application software module 54 executable on the central processor 40 is provided, where the beamformer application software module 54 includes a series of executable instructions, also referred to as a beamformer application, for controlling transfer of data between the high bandwidth memory 42 and the integrated module 56, and for controlling the interface module 14, and for performing beamforming transmit and/or receive processing on data written to and/or read from the integrated module 56. The beamforming processing performed by the beamformer application software module 54 may perform all of the beamforming processing performed in the ultrasound imaging system 10, or may perform partial beamforming processing, where a remainder of the beamforming processing is performed in other components of the ultrasound imaging system 10, such as by beamforming circuitry or a processor executing beamforming software provided in the other components of the ultrasound imaging system 10.

The high bandwidth memory 42 is connected by at least one high bandwidth connector, such as bus 60, to the central processor 40. Furthermore, the high bandwidth memory 42 is connected by high bandwidth connector 28 to the interface module 14. Coupling means, such as a bus, may be provided between the high bandwidth connector 28 and the high bandwidth memory 42. In order to maximize bandwidth between the high bandwidth memory 42 and the interface module 14, the high bandwidth connector 28 preferably connects directly to the high bandwidth memory, or the bus provided between the high bandwidth connector 28 and the high bandwidth memory 42 is kept short.

A communication link 62 is provided between the central processor 40 and the interface module 14 for transfer of control signals between the same. The control signals provide synchronization of data transfer between the central processor 40 and the interface module 14 via the integrated module 56. Communication links between processors are known in the art. Communication via communication link 62 may include, for example, communication via a cable and one of the I/O ports 48, or by writing and reading data from specifically allocated memory location(s) accessible by both processors, such as memory locations allocated in the high bandwidth memory 42 which are not accessible by the operating system.

Figure 2A:
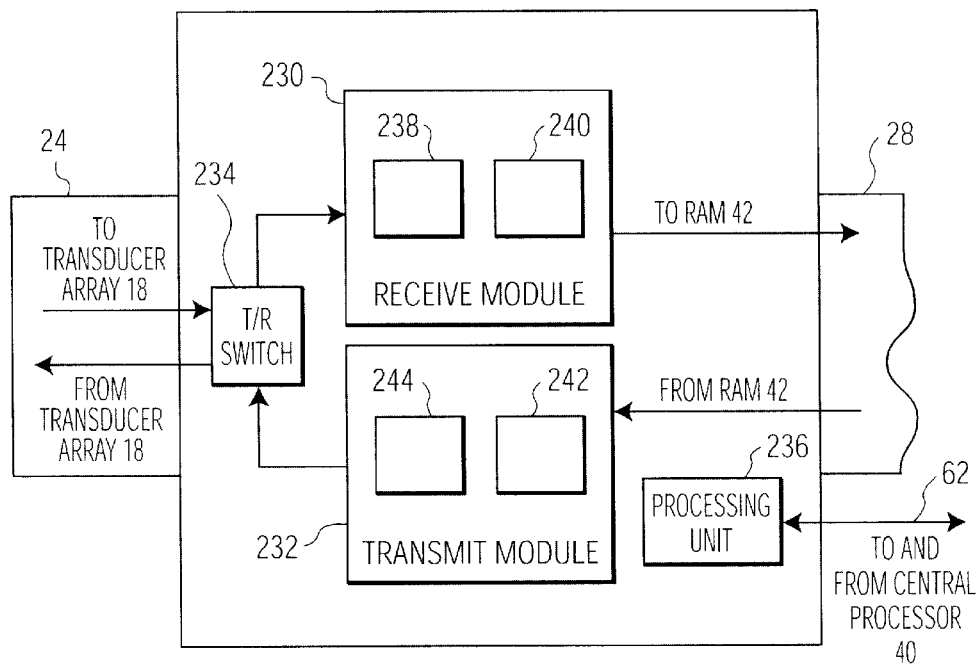
FIG. 2A is a block diagram of a interface module of the embodiment of FIG. 1.

FIG. 2A shows the interface module 14 in greater detail. With reference to FIG. 1 and FIG. 2A, the interface module 14 includes at least one of a receive module 230 and a transmit module 232. For embodiments in which the receive module 230 and transmit module 232 are both included in the interface module 14, switching means 234, such as a transmit/receive (T/R) switch or a multiplexer, is included for directing signals between the transducer array 18 and the respective receive module 230 and transmit module 232.

The interface module 14 further includes a processing unit 236 for controlling data transfer between the interface module 14 and the central processor 40 and/or for controlling operation of the interface module 14. The processing unit 236 is preferably a microprocessor, but may also be other processing means, such as an analog circuit or a logic circuit. When the processing unit 236 is a microprocessor, the microprocessor stores and executes executable instructions for performing prescribed functions. Preferably, the executable instructions are downloaded from the computing device 16 to the microprocessor during power-up of the microprocessor.

Control processing for generating the control signals transmitted between the central processor 42 and the interface module 14, as well as control signals for controlling internal functioning of interface module 14, is performed by either the central processor 40 or the processing unit 236, or a combination thereof. The control signals control, for example, switch means 234; execution of read and write operations performed by the interface module 14 and or the central processor 40; synchronization of data transfer between the interface module 14 and central processor 40 via the integrated module 56, including notification of data locations in high speed memory 42 and timing of data transfers; transitioning between transmit and receive modes of the interface module 14 and/or the central processor 40; and/or allocation of memory and/or notification of addresses of allocated memory within high bandwidth memory 42, or a combination thereof.

The receive module 230 includes, for example, RF preamplifiers 238, A/D converters 240, as well as memories and clock generation circuits (not shown) for digitizing echo signals, i.e., analog RF receive signals received from the probe 12, having sufficient bandwidth and dynamic range for subsequent beamforming operations to be performed at the computing device 16. During a receive cycle, the receive module 230 receives a collection of analog RF receive signals, and converts the analog RF signals into Digital RF signals, and writes the Digital RF signals into designated locations receive in high bandwidth memory 42.

The transmit module 232 includes, for example, memories and clock circuits (not shown), D/A converters 242, high voltage RF amplifiers 244 for individually driving the transducer elements for generating acoustic signals. During a transmit cycle, the transmit module 232 reads digital beamformed transmit data from designated locations in high bandwidth memory 42, converts the digital beamformed transmit data into analog beamformed transmit data, and transmits the analog beamformed transmit data to the transducer array 18 via cable 20.

Figure 2B:
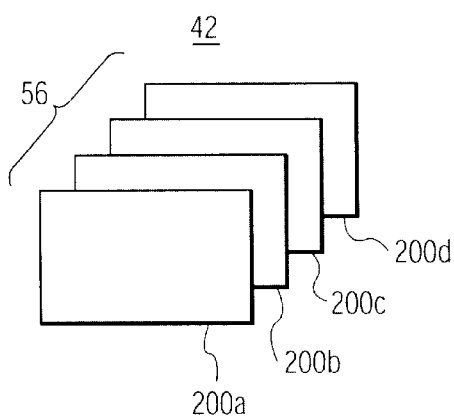
FIG. 2B is a schematic representation of random access memory (RAM) provided in the embodiment of FIG. 1.

FIG. 2B shows the high bandwidth memory 42 in greater detail. The high bandwidth memory 42 is preferably provided with at least a dual port function configured for supporting access to the high bandwidth memory 42 by two users, i.e. the central processor 40 and the interface module 14. The dual port function is provided by two physical ports, or by one port controlled to act as two ports. The high bandwidth memory 42 is exemplified in FIG. 2B to be a RAM, which may include single port or dual port RAM cards or chips (hereinafter referred to as cards) 200a–d, however it is to be understood that additional RAM cards may be included, or that a RAM card may be apportioned to allocate specific portions of the RAM card to perform the functions described for one or more of the cards 200a–d. Addresses of RAM cards 200a–d may be allocated for the specified functions physically or dynamically. RAM card 200a is preferably a commercially available RAM originally installed prior to installation of the integrated module. RAM card 200a is connected to the central processor 40 for high speed data transfers via bus 60 having a high bandwidth.

The integrated module 56 includes RAM cards 200b–d in the example shown in FIG. 2B. A portion of the high bandwidth memory 42, i.e., RAM cards 200b–d in this example, is allocated for the integrated module 56. Alternatively, the integrated module 56 is an allocated portion of RAM card 200a. The integrated module 56 is installed within the computing device 16 in the same way that additional RAM is added when upgrading the RAM of a computing device, as is known by one skilled in the art. Upon installation of RAM cards 200b–d, the RAM cards 200b–d are connected to the central processor 40 via bus 60. Preferably bus 60 is a standard interface for RAM and a central processor.

RAM cards 200a–d together form the high bandwidth memory 42, where each location in each of the high bandwidth memory cards 200a–d has a unique address. The RAM card 200a is accessed by the operating system of the computing device 16. The operating system controls swapping of information, such as data and executable programs in and out of RAM card 200a, allocating addresses to information stored in RAM card 200a.

The integrated module 56, i.e., RAM cards 200b–d, is accessed by the central processor 40 upon execution of the beamformer application software module 54. The beamformer application software module 54 specifically includes a series of executable instructions for performing read and/or write operations on the integrated module 56 by the central processor 40. The addresses occupied by the integrated module 56 are unavailable to the operating system. The operating system is restricted from using the addresses allocated to the integrated module 56 for use by the beamformer application software module 54. Preferably, the operating system is a commercially available operating system which can be programmed or customized to access only a first subset, of the RAM address locations available, while allowing an application running on the operating system to access only a second subset of the RAM address locations available which is mutually exclusive from the first subset.

The beamformer application software module 54 includes at least one of a beamformer transmit application module 54a and a beamformer receive application module 54b. For a beamformer application software module 54 that includes both beamformer transmit and receive application modules 54a,b, the integrated module 56 is further divided into a transmit RAM address subset and a receive RAM address subset, to which access is only allowed by the beamformer transmit and receive application modules 54a,b, respectively. In the exemplary RAM shown in FIG. 2B, the addresses for the locations of RAM card 200b are allocated to exclusive use by the beamformer transmit application module 54a, and the addresses for the locations of RAM cards 200c–d are allocated to exclusive use by the beamformer receive application module 54b.

During the receive mode, the beamformer receive application module 54b of interface module 14 writes a first line of digital RF data into the integrated module 56 in a first set of designated locations of the receive RAM address subset, each channel of digital RF data being stored in a predetermined address range. The beamformer receive application module 54b reads the first line of digital RF data and performs receive beamforming processing on the digital RF data, including performing delay and summation processing, to generate receive beamformed data. Preferably, a next line of digital RF data is written into a second set of designated locations of the receive RAM address subset. Each subsequent line of received digital RF data is written alternately into the first and second sets of designated locations, so that while processing is being formed on data stored in one of the first and second sets of designated locations, received digital RF data is being stored in the other designated location.

The receive beamformed data is processed for display, such as by a display module of the beamformer software application module 54 or by a display application, for performing processes, such as, RF filtering, detection, color flow and Doppler detection, and scan conversion to rectangular coordinate format for display on a graphical monitor, as is known in the art. The receive beamformed data may be stored in the integrated module 56 for access by the display module or display application.

The inventive beamformer includes at least one of a transmit beamformer or a receive beamformer. The transmit beamformer includes at least the beamformer transmit application module 54a, RAM card 200b, transmit module 232, processing unit 236, communication link 62, and cable 20 for providing data and signal transmission in the direction shown in FIG. 1 for the transmit mode. The receive beamformer includes at least the beamformer receive application module 54b, RAM cards 200c and 200d, receive module 230, processing unit 236, communication link 62, and cable 20 providing data and signal transmission in the direction shown for the receive mode.

Figure 3:
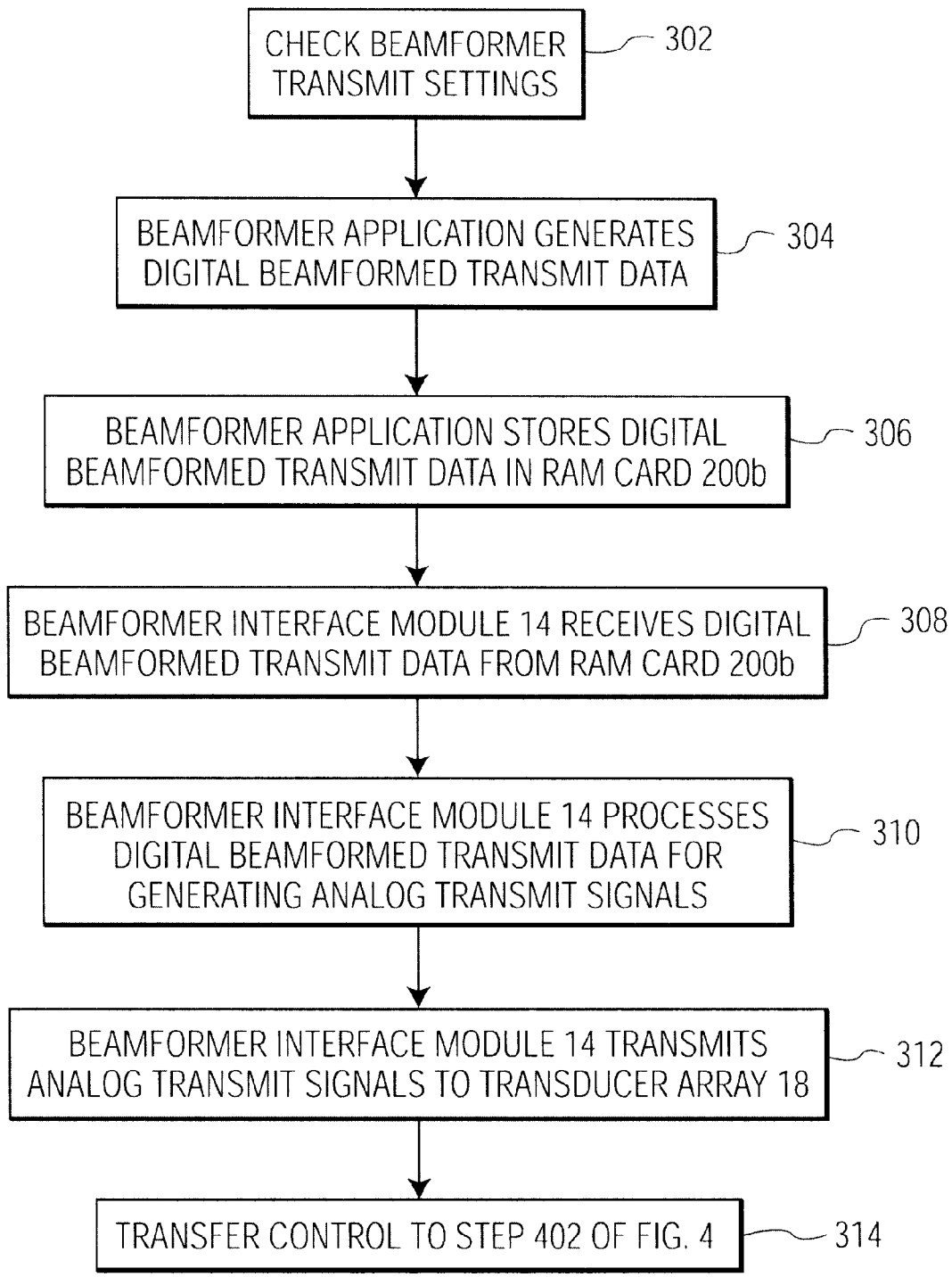
FIG. 3 is a flow diagram of performance steps performed by a transmit portion of the beamformer in accordance with the present invention.

FIG. 3 shows performance steps performed by the transmit beamformer during the transmit mode. At step 302, the beamformer application software module 54 checks beamformer transmit settings, which may be default or user entered values entered at initialization or during an imaging procedure, for selecting a desired mode of scanning, such as by selecting transmit waveforms and focusing parameters At step 304, the beamformer transmit application module 54a determines from user entered parameters the scanning sequences and transmit waveforms which need to be performed by the transducer array 18, performs transmit beamforming processing, including computing and applying appropriate delays respectively to each channel, and generates digital beamformed transmit data representing the selected scanning sequences and transmit waveforms and focal point. At step 306, the beamformer transmit application module 54a stores the digital beamformed transmit data in the addresses of the RAM 42 (RAM card 200b in this example) allocated to use by the beamformer transmit application module 54a.

At step 308, processing unit 236 is notified by the central processor that new digital beamformed transmit data is stored in RAM 42, and the processing unit 236 initiates a read operation for reading the digital beamformed transmit data from the allocated addresses in RAM 200b. At step 310, the interface module 14 processes the digital beamformed transmit data for converting the digital beamformed transmit data into analog beamformed transmit signals. The digital beamformed transmit data typically represents selected waveforms in accordance with focusing selections selected by user's settings or default values. The analog beamformed transmit signals are collections of individual electrical signals in the form of pulses for exciting the respective transducer elements. At step 312 the interface module 14 transmits the analog beamformed transmit signals via cable 20 to the transducer array 18. At step 314, control is transferred to step 402 of FIG. 4 for transitioning to the receive mode for receiving RF echo signals from the transducer array 18.

Figure 4:
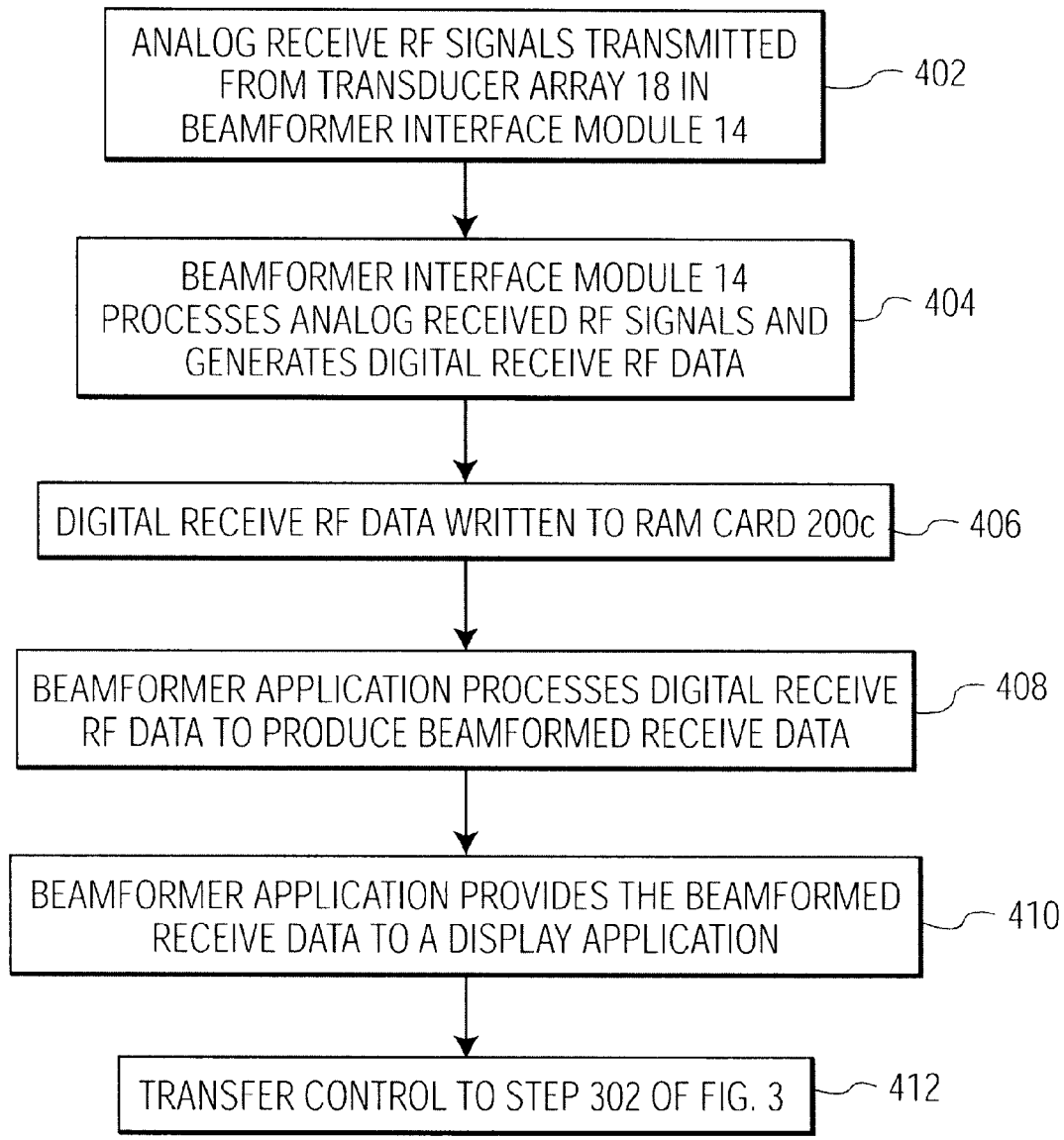
FIG. 4 is a flow diagram of performance steps performed by a receive portion of the beamformer in accordance with the present invention.

FIG. 4 shows operation of the receive beamformer during the receive mode. Once the transducer array has begun transmission of acoustic energy, at step 402 real time analog RF receive signals are transmitted from the transducer array 18 via cable 20 to the interface module 14. At step 404, in interface module 14, the analog RF receive signals are pre-amplified and converted from analog signals to digital RF receive data. At step 406, the digital RF receive data is written, substantially in real time via connector 28, to RAM card 200c for storage. Processing unit 236 notifies central processor 40 that new digital RF receive data is stored in RAM 42. At step 408, the beamformer application software module 54 performs beamforming and signal processing algorithms on the digital RF receive data stored in RAM 200c, and generates digital beamformed receive data. At step 410, the digital beamformed receive data is processed for display, such as on a monitor. At step 412 control is transferred to step 302 of FIG. 3. Subsequent lines of received data are stored and processed alternately in RAM cards 200c and 200d.

The beamformer of the present invention provides high bandwidth capabilities, the ability for the beamformer application software module 54 to be usable across several hardware generations and the ability to test and develop new prototype beamformer software applications without implementing new hardware configurations. Furthermore, by performing beamforming processing in a processor, the output of the beamformer processing may be provided in display coordinates, rather than in acoustic coordinates as typically provided by conventional beamformers, therefore eliminating the need to convert between acoustic coordinates and display coordinates.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A beamformer for an ultrasound imaging system, the ultrasound imaging system including a probe having a transducer array for transmitting and receiving analog RF signals, and a computing device, said beamformer comprising:

a beamformer software application module configured for execution by the computing device for performing at least partial beamforming processing on digital data transmitted between the transducer array and the computing device;

means for exchanging signals and data between the transducer array and the computing device and performing at least one of A/D and D/A conversions on the exchanged signals and data;

storage means integrated within an architecture of the computing device and having a subset of storage address locations available for an integrated module, the integrated module for storing data exchanged between the computing device and said means for exchanging signals and data; and means for allocating the integrated module for exclusive use by the beamformer software application module for at least one of a transmit and a receive beamformer application.

2. The beamformer in accordance with claim 1, wherein the means for exchanging signals includes an interface module coupled between the transducer array and the computing device for performing the conversions.

3. The beamformer in accordance with claim 2, wherein the beamformer interface module includes a transmit module comprising:

means for receiving the digital data from the computing device;

means for converting the digital data to analog signals; and means for transmitting the analog signals to the transducer array.

4. The beamformer in accordance with claim 2, wherein the beamformer interface module includes a receive module comprising:

means for receiving the analog signals from the transducer array;

means for converting the analog signals to digital data; and means for transmitting the digital data to the computing device.

5. The beamformer in accordance with claim 2, wherein at least one of the computing device and the interface module includes means for generating control signals for synchronizing data exchange between the computing device and the interface module; and wherein the beamformer further comprises a communication link providing communication between the computing device and the interface module for propagating the control signals.

6. The beamformer in accordance with claim 5, wherein the beamformer further includes a module integrated within architecture of the computing device for storing digital signals exchanged between the computing device and the beamformer integrated module, and wherein the control signals synchronize data exchange between the computing device and the interface module via the integrated module.

7. The beamformer in accordance with claim 5, wherein the beamformer software application module includes means for generating a second set of control signals for controlling the interface module, and wherein the second set of control signals are transmitted via the communication link.

8. The beamformer in accordance with claim 1, wherein the integrated module is Random Access Memory (RAM).

9. The beamformer in accordance with claim 1, wherein the integrated module is configured for supporting access by both the computing device and an external module, the external module including at least one of a transmit module and a receive module.

10. The beamformer in accordance with claim 1, wherein the storage means of the computing device is interfaced with a central processor of the computing device via an interface, and wherein the integrated module is interfaced to the central processor via the interface.

11. The beamformer in accordance with claim 1, wherein the computing device is a personal computer, the storage means is a Random Access Memory (RAM) Module, and the integrated module is included in the RAM module.

12. The beamformer in accordance with claim 1, wherein the beamformer includes means for selecting transmit settings; and wherein the beamformer application software module includes means for performing transmit beamforming processing on selected transmit settings for generating digital beamformed transmit signals; and means for writing the digital beamformed transmit signals in the integrated module.

13. The beamformer in accordance with claim 1, wherein the beamformer application software module includes means for performing receive beamforming processing on analog signals transmitted by the transducer array which were converted to digital data and exchanged with the computing device by the means for exchanging signals.

14. A beamformer for an ultrasound imaging system, the ultrasound imaging system including a probe having a transducer array for transmitting and receiving analog signals, and a computing device having at least storage memory and a central processor coupled to the storage memory, said beamformer comprising:

an interface module coupled to the transducer array of the probe and to the storage memory for propagating signals between the transducer array and the interface module and for transmitting data between the interface module and a selected portion of the storage memory;

a beamformer software application module configured for execution by the central processor for performing at least partial beamforming processing on the data transmitted between the interface module and the selected portion of the storage memory, wherein the selected portion of the storage memory includes a subset of storage address locations available for an integrated module, the integrated module for storing data exchanged between the interface module and the selected portion of the storage memory; and means for allocating the integrated module for exclusive use by the beamformer software application module for at least one of a transmit and a receive beamformer application.

15. The beamformer in accordance with claim 14, wherein the storage memory of the computing device includes Random Access Memory (RAM), and the selected portion of the storage memory is included in the RAM.

16. The beamformer in accordance with claim 14, wherein the beamformer interface module includes means for exchanging signals and data between the transducer array and the selected portion of the memory and performing at least one of A/D and D/A conversions on the exchanged signals.

17. A method for performing a transmit beamforming process in an ultrasound system having a computing device and a probe including a transducer array, the method comprising the steps of:

allocating an integrated module within the computing device for exclusive use by a beamformer software application module for a transmit beamformer application;

performing transmit beamforming processing in the computing device in accordance with user entered transmit settings to generate digital beamformed transmit data;

storing the digital beamformed transmit data in a storage memory, the storage memory being integrated within an architecture of the computing device and having a subset of storage address locations available for the integrated module, the integrated module for storing data exchanged between the computing device and the probe for exchanging signals and data;

retrieving the digital beamformed transmit data from the storage memory;

converting the digital beamformed transmit data to analog transmit signals; and transmitting the analog transmit signals to the transducer array.

18. A method for performing a receive beamforming process in an ultrasound system having a computing device including storage memory, an interface module and a probe including a transducer array, the method comprising the steps of:

allocating an integrated module within the computing device for exclusive use by a beamformer software application module for a receive beamformer application;

receiving analog RF receive signals from the transducer array;

converting the analog RF receive signals to digital RF receive data;

storing the digital RF receive data in the storage memory, the storage memory being integrated within an architecture of the computing device and having a subset of storage address locations available for the integrated module, the integrated module for storing data exchanged between the computing device and the probe for exchanging signals and data;

retrieving the digital RF receive data from the storage memory; and performing receive beamforming operations on the digital RF receive data by the computing device.

19. An interface module of an ultrasound imaging system having a transducer array for transmitting and receiving analog RF signals, and a computing device that executes beamforming software for performing at least partial beamforming processing on digital data transmitted between the transducer array and the computing device, the interface module comprising:

means for exchanging signals and data between the transducer array and the computing device via a storage memory, wherein a selected portion of the storage memory includes a subset of storage address locations available for an integrated module, the integrated module for storing data exchanged between the interface module and the selected Portion of the storage memory;

means for allocating the integrated module for exclusive use by a beamformer software application module for at least one of a transmit and a receive beamformer application; and means for performing at least one of A/D and D/A conversions on the exchanged signals and data.

20. A beamformer application software module executable on a computing device of an ultrasound imaging system having a transducer array for transmitting and receiving analog RF signals, the computing device, and an interface module for exchanging signals and data between the transducer array and the computing device, and for performing at least one of A/D and D/A conversions on the exchanged signals and data, the beamformer software application module comprising:

executable beamforming software for performing at least partial beamforming processing on digital data transmitted between the transducer array and the computing device;

means for synchronizing the exchange of signals between the interface module and the computing device; and means for allocating an integrated module of a storage means for exclusive use by a beamformer software application module for at least one of a transmit and a receive beamformer application.

* * * * *